US00RE41898E

(19) United States
(12) Reissued Patent
Huang et al.

(10) Patent Number: US RE41,898 E
(45) Date of Reissued Patent: Oct. 26, 2010

(54) PROCESS FOR HALOMETHYL ETHERS OF HYDROXYIMINOMETHYL QUATERNARY PYRIDINIUM SALTS

(75) Inventors: Der-Shing Huang, Folsom, CA (US); George R. Gettys, Citrus Heights, CA (US); Olivier Dapremont, Citrus Heights, CA (US)

(73) Assignee: Aerojet Fine Chemicals LLC, Rancho Cordova, CA (US)

(21) Appl. No.: 12/274,133

(22) Filed: Nov. 19, 2008

Related U.S. Patent Documents

Reissue of:
(64) Patent No.: 7,414,135
Issued: Aug. 19, 2008
Appl. No.: 11/133,740
Filed: May 19, 2005

U.S. Applications:

(63) Continuation-in-part of application No. 11/061,064, filed on Feb. 17, 2005, now abandoned.

(51) Int. Cl.
*C07D 401/02* (2006.01)

(52) U.S. Cl. ..... 546/256; 546/329
(58) Field of Classification Search ..... None
See application file for complete search history.

(56) References Cited

U.S. PATENT DOCUMENTS

| | | | | | |
|---|---|---|---|---|---|
| 3,137,702 | A | * | 6/1964 | Luttringhaus et al. | 546/264 |
| 3,773,775 | A | * | 11/1973 | Hagedorn | 546/262 |
| 3,852,294 | A | * | 12/1974 | Hagedorn | 546/264 |
| 4,128,651 | A | * | 12/1978 | Hagedorn | 514/332 |
| 4,677,204 | A | * | 6/1987 | Sommer et al. | 546/261 |
| 5,130,438 | A | * | 7/1992 | Hsiao et al. | 546/262 |
| 2006/0183777 | A1 | * | 8/2006 | Huang et al. | 514/334 |

OTHER PUBLICATIONS

Dirks et al, 1970, Arneim. Forsch. vol. 20, No. 1, pp. 55–62.*

Yang et al., 2003, Bull, Korean Chem. Soc., vol. 24, No. 9, pp. 1368–1370.*

Eyer et al., 1992, Arch Toxicol, vol. 66, No. 9, pp. 603–621.*

Hagedorn et al., 1978, Arzneim–Forsch., vol. 28, No. 11, pp. 2055–2057.*

Yang, Garp Yeol et al.; "Synthesis of Bis–pyridinium Oxime Anti–dotes Using Bis(methylsulfonoxymethyl) Ether for Organophosphate Nerve Agents"; 2003, *Bull. Korean Chem. Soc.,* vol. 24, No. 9, pp. 1368–1370.

Dirks, E. et al.; "Beziehung zwischen chemischer Struktur und Cholinesterase–reaktivierender Wirkung bei einer Reihe neuer unsymmetrischer Pyridinumsalze"; 1970, *Arneim Forsch,* vol. 20, No. 1, pp. 55–62.

Eyer, P. et al.; "HLo7 dimethanesulfonate, a potent bispyridinium–dioxime against anticholinesterases"; 1992, *Arch Toxicol,* vol. 66, No. 9, pp. 603–621.

Hagedorn, Von I. et al.; "Reaktivierung phosphorylierter Acetylcholin–Esterase"; 1978, *Arzneim–Forsch.,* vol. 28, No. 11, pp. 2055–2057.

* cited by examiner

*Primary Examiner*—Zinna N Davis
(74) *Attorney, Agent, or Firm*—Townsend and Townsend and Crew LLP.; M. Henry Heines

(57) ABSTRACT

A halide salt of a 1-(hydroxyiminomethyl-1-pyridino)-3-(halomethyl)-2-oxapropane is prepared by adding a pyridinealdoxime to a bis-halomethylether in such a manner that the bis-halomethylether is maintained in excess throughout the addition. This procedure produces the halide salt of a 1-(hydroxyiminomethyl-1-pyridino)-3-(halomethyl)-2-oxapropanein high yield and purity, which facilitates its use as an intermediate in the manufacture of an asymmetrically substituted 1,3-di(1-pyridino)-2-oxapropane, a class of compounds that are generally useful antidotes to various toxic agents. A prominent member of the class is the dimethylsulfonate salt of 1-(2-hydroxyiminomethyl-1-pyridino)-3-(4-carbamoyl-1-pyridino)-2-oxapropane. The use of mercaptoalkyl-functionalized polymers is disclosed as a preferred metal ion scavenger for a final purification step in the manufacture of these compounds.

22 Claims, No Drawings

PROCESS FOR HALOMETHYL ETHERS OF HYDROXYIMINOMETHYL QUATERNARY PYRIDINIUM SALTS

Matter enclosed in heavy brackets [ ] appears in the original patent but forms no part of this reissue specification; matter printed in italics indicates the additions made by reissue.

CROSS REFERENCE TO RELATED APPLICATION

This application is a *Reissue of Ser. No. 11/133,740 filed May 19, 2005, now U.S. Pat. No. 7,414,135 which is a* continuation-in-part of, and claims benefit from, U.S. patent application Ser. No. 11/061,064, filed Feb. 17, 2005, now abandoned. The contents of the aforesaid patent application are hereby incorporated herein by reference for all purposes capable of being served thereby.

BACKGROUND OF THE INVENTION

1. Field of the Invention

This invention resides in the field of process chemistry for the N-alkylation of pyridinealdoximes. In particular, this invention addresses processes for the preparation of intermediates for the synthesis of asymmetrical dipyridinomethyl ethers.

2. Description of the Prior Art

The bis-quaternary salts of certain dipyridinomethyl ethers are known to be effective antidotes for toxic agents that are known in the military as nerve gases as well as for certain insecticides. These antidotes are thus useful to the military, the agricultural industry, and the home gardener, and in general any location or application where there is a risk of exposure to the toxic agents.

The most potent of the antidotes in this class are those with asymmetrical structures, i.e., those in which one or more substituents are present on one of the two pyridine rings and not the other, or the substituent(s) on one of the two pyridine rings differ in either structure or position from those on the other. Unfortunately, antidotes with asymmetrical structures are difficult to manufacture, with known synthesis routes tending to produce low yields and high levels of undesired. An illustration of the difficulty is found in U.S. Pat. No. 5,130,438 (Hsiao, L. Y. Y, et al., Jul. 14, 1992, entitled "Bis-Methylene Ether Pyridinium Compound Preparation"). The product mixtures in this patent include the desired asymmetrical ether together with symmetrical ethers and quaternary salts of the pyridinium compounds that are used as starting materials. One of the most potent compounds disclosed in the patent is 1-(2-hydroxyiminomethyl-1-pyridino)-3-(4-carbamoyl-1-pyridino)-2-oxapropane (commonly known as "HI-6"), shown as both the dichloride and dimethanesulfonate salts. This compound is only one of four reaction products in the product mixture, however, and recovery of the desired compound requires a lengthy isolation procedure involving multiple recrystallizations and resulting in a low yield. Other disclosures of potential relevance to this invention are U.S. Pat. No. 3,773,775 (Hagedorn, I., Nov. 20, 1973, entitled "Bis-Quaternary Pyridinium Salts") and U.S. Pat. No. 3,852, 294 (Hagedorn, I., Dec. 3, 1974, entitled "Bis-Quaternary Pyridinium Salts"). All patents and other literature cited in this specification is hereby incorporated herein by reference.

SUMMARY OF THE INVENTION

It has now been discovered that the yield of salts of asymmetrical 1-(hydroxy-iminomethyl-1-pyridino)-3-(substituted-1-pyridino)-2-oxapropanes, which as a class are antidotes of the toxic agents discussed above, as well as the purity of these compounds, can be increased by modifying the manufacturing process to form a salt of a 1-(hydroxy-iminomethyl-1-pyridino)-3-(halomethyl)-2-oxapropane as an intermediate by adding a pyridinealdoxime to a bis-halomethylether in such a manner that the bis-halomethylether is maintained in excess throughout at least most of, and preferably all, of the addition. This procedure is distinct from that of the prior art, particularly the disclosures of Hagedorn cited above, in which a reverse addition procedure is used, i.e., the bis-halomethylether is added to the pyridinealdoxime, and this invention achieves a significant and surprising improvement in both product yield and product purity. This invention thus resides in a process for the preparation of salts of asymmetrical 1,3-di-(1-pyridino)-2-oxapropanes, as well as a process for the preparation of the intermediates. Further objects, advantages, and aspects of this invention will be apparent from the descriptions that follow.

It has also been discovered that dimethanesulfonate salts of 1,3-di-(1-pyridino)-2-oxapropanes can be purified to a particularly high degree from a product mixture containing metallic methanesulfonate salts by contacting a liquid solution of said product mixture with an insoluble mercaptoalkyl-functionalized polymer. The resulting purity is unexpectedly greater than the purity achieved by the use of other purifying media.

DETAILED DESCRIPTION OF THE INVENTION AND PREFERRED EMBODIMENTS

The antidotes that are the end product of the processes of this invention are represented by the formula (I)

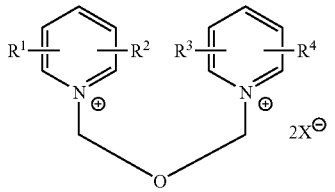

In this formula, the symbol $R^1$ represents —CH═NOH, and the symbols $R^2$, $R^3$, and $R^4$ independently represent either H, lower alkyl, —C(O)—O-(lower alkyl), —C(O)—$NH_2$, or —CH═NOH, provided that the selection of the substituents, their arrangement on the pyridine rings, or both, result in an asymmetric structure. The term "asymmetric" in this specification and the appended claims denotes that the substituents are such that the two pyridino rings differ from each other, either because one is substituted and the other is not, or because a substituent appears on one that does not appear on the other, or the ring vertices to which the various substituents are bonded differ between the two rings, or a combination of these differences. The term "independently selected" is used herein to denote that $R^2$, $R^3$, and $R^4$ can be all the same, all different, or two the same and the third different.

The alkyl groups are either linear or branched, and preferred lower alkyls are $C_1$-$C_3$ alkyl, preferably linear, and most preferably $CH_3$. Preferred among the $R^1$ groups are —C(O)—O-(lower alkyl), —C(O)—$NH_2$, and —CH═NOH other than 2-CH═NOH. Also preferred are lower alkyl, —C(O)—O-(lower alkyl), —C(O)—$NH_2$ in the 4-position (i.e., the para-position) on the pyridine ring. More preferred are —C(O)—O-(lower alkyl) and —C(O)—$NH_2$, and the most preferred is —C(O)—$NH_2$, particularly 4-C(O)—$NH_2$.

The symbol X represents any atom or group capable of forming a pharmaceutically acceptable anion. Preferred examples are halides, hydrocarbyl sulfonates, and halohydrocarbyl sulfonates, of the generic formula $R^5SO_3^-$. Of the halides, Br and Cl are preferred, and Cl is the most preferred. Of the sulfonates, aliphatic and aromatic sulfonates are included, with preferred sulfonates being those in which $R^5$ is $C_1$—$C_4$ alkyl, halo($C_1$—$C_4$ alkyl), cyclohexyl, or phenyl, and the most preferred is that in which $R^5$ is methyl or halomethyl. The sulfonate in which $R^5$ is methyl is referred to herein as methanesulfonate.

The intermediate of interest in this invention is a 1-(hydroxyiminomethyl-1-pyridino)-3-(halomethyl)-2-oxapropane, halide salt, whose formula is (II)

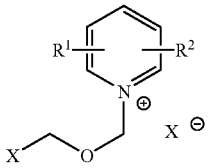

wherein X is a halogen atom. Conversion of this intermediate to the antidote of Formula (I) will result in a product in which the anion X is the same halogen atom. This anion can be exchanged for other anions, including dimethanesulfonate and the other pharmaceutically acceptable anions, by ion exchange, as will be demonstrated below.

Addition of the pyridinealdoxime to bis-halomethylether is achieved such that the unreacted bis-halomethylether remains in stoichiometric excess for most, if not all, of the addition. This is preferably achieved by adding the pyridinealdoxime to a body of the bis-halomethylether at a slow rate with continuous agitation. Dropwise addition is one means of accomplishing this result. The excess of unreacted bis-halomethylether is preferably maintained for at least until 75% of the pyridinealdoxime has been added, more preferably until at least 90% has been added, and most preferably throughout the entire addition.

The bis-halomethylethers are known compounds, commercially available and disclosed for example in the Hsiao et al. and Hagedorn patents cited above, as well as U.S. Pat. No. 3,137,702 (Lüttringhaus, A., et al., Jun. 6, 1964, entitled "Preparation of Bis-Quaternary Pyridinium Salts"). Bis-chloromethylether for example can be prepared by reaction of paraformaldehyde with hydrochloric acid and chlorosulfonic acid.

The bis-halomethylether is in the liquid phase during the addition of the pyridinealdoxime, and this can be achieved by using the ether in neat form since it is a liquid at ambient temperature and any elevated temperatures at which the reaction might be performed, or the ether can be dissolved in a solvent. If a solvent is used, any conventional solvent that is inert to the reaction will suffice. Examples are tetrahalomethanes, dimethylformamide, trihalomethanes, dihalomethanes, N,N-dimethylacetamide, 1-methyl-2-pyrrolidone, acetonitrile, dioxane, tetrahydrofuran, and 2-methyltetrahydrofuran.

Conversion of the intermediate (II) to the product asymmetrical 1,3-di-(1-pyridino)-2-oxapropane (I) is achieved by reacting the intermediate with a substituted pyridine of the formula (III)

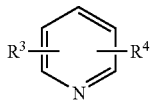

in which $R^3$ and $R^4$ are as defined above. This reaction is likewise performed in a liquid reaction medium, and a solvent can be used if desired. The solvents listed above are examples of solvents that can be used in this reaction as well.

Of the compounds employed in the processes of these invention and expressed generically above, certain subgenera are preferred. One preferred subgenus of pyridinealdoximes, for example is that represented by the formula

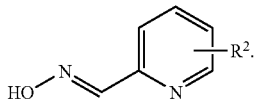

Another preferred subgenus is that represented by the formula

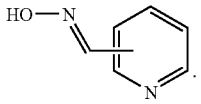

A particularly preferred pyridinealdoxime is 2-pyridinealdoxime, whose formula is

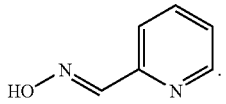

Regarding the substituted pyridines of Formula (III), one preferred subgenus is that represented by the formula

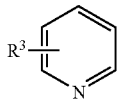

Another is that represented by the formula

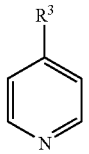

A third is that represented by the formula

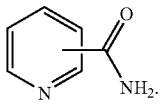

A particularly preferred substituted pyridine is 4-carbamoylpyridine of the formula

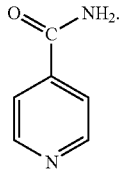

Both reactions can be conducted in batch-wise or continuous manner, provided that the reaction to form the intermediate (II) is performed with a continuous excess of the bis-halomethyl ether for most, if not all, of the duration of the reaction. The reaction to form the intermediate (II) is preferably accompanied by agitation, and can be performed at ambient temperature but is preferably performed at an elevated temperature of from about 30° C. to about 100° C., or most preferably from about 35° C. to about 60° C. The reaction between the intermediate (II) and the substituted pyridine (III) can likewise be performed at ambient temperature but is preferably performed at an elevated temperature within the same ranges. Both reactions can be performed at atmospheric pressure or slightly above or below. Both reactions can be performed in air or in an inert atmosphere such as nitrogen or argon.

Reaction products at either stage can be isolated by conventional means. Liquid products can thus be recovered by conventional phase separation, including decantation and centrifugation, and solid products can be recovered by filtration or centrifugation. Conversion of the chloride salts to salts of other anions, including methanesulfonate (which is also referred to as "mesylate"), can be achieved by ion exchange. The ion exchange may be performed with metallic salts such as silver methanesulfonate, sodium methanesulfonate, and calcium methanesulfonate, or common ion exchange resins, all of which are commercially available.

As noted above, one of the products that can be synthesized by the methods of this invention is 1-(2-hydroxyiminomethyl-1-pyridino)-3-(4-carbamoyl-1-pyridino)-2-oxapropane (commonly known as "HI-6") methanesulfonate salt, a highly effective anti-nerve agent. The synthesis of this product is most successful when the metallic salt used is silver methansulfonate. It is also preferable, for reasons of both solubility and toxicity, that any heavy metallic ions, such as $Ag^+$ ions, be in a low concentration when such ions are present in the reaction system.

As also noted above, functionalized polymers, and notably mercaptoalkyl-functionalized polymers, have been found to be a particularly effective class of metal scavenging media for the isolation of dimethanesulfonate salts of 1,3-di-(1-pyridino)-2-oxapropanes from metallic methanesulfonate salts. This quality makes these polymers particularly useful in product purification procedures following the conversion of dihalide salts of the 1,3-di-(1-pyridino)-2-oxapropanes to dimethylsulfonate form. Examples of these polymers are silica gels, polyolefins, polystyrene, polyvinyl alcohol, polyepichlorohydrin, polyoxetane, and crosslinked polyalkyl fiber, all functionalized with mercaptoalkyl groups. Preferred among the mercaptoalkyl functional groups are mercapto-($C_1$-$C_5$ alkyl) groups, more preferred are mercapto-($C_2$-$C_4$ alkyl) groups, and the most preferred is mercaptopropyl. The metal ions that these polymers are effective in removing include $Ag^+$, $Hg^{++}$, $Pd^{++}$, and $Pt^{4+}$ ions. For the purposes of the present invention, the polymers are of particular interest in removing $Ag^+$ ions. Mercaptopropyl-functionalized silica gel is one example. Other silica gels that are efficient $Ag^+$ ion scavengers and can be used herein are silica gels bonded with triaminetetraacetic acid groups (SiliaBond TAAcOH) and propylthiourea groups (SiliaBond Thiourea), both of which are commercially available from Silicycle, Inc., Quebec, Canada. Examples of functionalized polyalkyl fibers that are known to be effective in removing $Ag^+$ ion are polyalkyl fibers functionalized with benzylthio groups (SMOPEX®-111x), isothionium groups (SMOPEX®-112x) and mercaptoethyl acrylate groups (SMOPEX®-234x), all of which are commercially available from Johnson Matthey plc., United Kingdom. The metal scavenging can be performed either by stirring the scavenger medium in the reaction mixture or by pumping the reaction mixture through one or several columns packed with the scavenger medium, with the columns connected either in series or in parallel. The metal scavenging can be performed in a continuous manner using a scavenging unit similar to a continuous catalytic reactor. Metal scavenging can be performed at any temperature within the range of 0° C. to 150° C., using conventional heating or microwave heating. Metal scavenging can also be enhanced in certain cases by the use of ultrasound.

The dimethanesulfonate salts of 1,3-di-(1-pyridino)-2-oxapropanes that are purified in this manner include salts of both substituted and unsubstituted 1,3-di-(1-pyridino)-2-oxapropanes, symmetrical and asymmetrical, and the preferred 1,3-di-(1-pyridino)-2-oxapropanes are those listed above as preferred embodiments for the synthesis reactions described herein.

The following examples are offered for purposes of illustration only.

EXAMPLE 1

Comparative Study: Preparation of 1-(2-Hydroxyiminomethyl-1-Pyridino)-3-(Chloromethyl)-2-Oxapropane, Chloride Salt, by Process of This Invention vs. Process of the Prior Art This example compares the yield and purity of 1-(2-hydroxyiminomethyl-1-pyridino)-3-(chloromethyl)-2-oxapropane, chloride salt as obtained by the process of the present invention with the yield and purity as obtained by the reverse order of reactant addition as disclosed in Hagedorn, I., et al., U.S. Pat. No. 3,773,775, Example 10. The structure of 1-(2-hydroxyiminomethyl-1-pyridino)-3-(chloromethyl)-2-oxapropane, chloride salt is as follows:

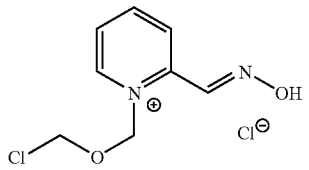

For both procedures, bis-chloromethylether was prepared by first cooling a mixture of paraformaldehyde (21.1 g, 0.7 mole) and 37% hydrochloric acid (16.7 g ) to 10° C., then slowly adding chlorosulfonic acid (55.1 g, 0.6 mole) and stirring overnight. The phases were then separated to obtain bis-chloromethylether as the neat liquid. The procedure used for this paragraph is described in Buc, S. R., Organic Syntheses, Collective Volume IV: pp. 101-103, 1963.

Following the process of the invention, pyridine-2-aldoxime (27.7 g, 0.23 mole) dissolved in chloroform (119.4 g) was then added to the bis-chloromethylether in dropwise manner over a period of 60 minutes (by adding one drop of pyridine-2-aldoxime approximately every second) at 45° C. with continuous stirring. Once the addition was completed, stirring was continued for three hours at the same temperature. The reaction mixture was then cooled to 18° C., and the product was filtered, washed with chloroform (66 g), and vacuum dried at 40° C. The product was identified by proton NMR as 1-(2-hydroxyiminomethyl-1-pyridino)-3-(chloromethyl)-2-oxapropane, chloride salt, plus the bis-impurity 1,3-di-(2-hydroxyiminomethyl-1-pyridino)-2-oxapropane.

$^1$H-NMR (300 MHz, $D_2O$): mono-product: δ (6.18 (s, 2H, —$CH_2O$), and 6.28 (2H)), bis-impurity: 6.48 (s, 4H, —$CH_2OCH_2$—). The yield was 78.7%, and from the NMR analysis, the product purity was 97.3%, with the bis-impurity as the remainder.

Following the process of Hagedorn et al., the bis-chloromethylether (28.7 g, 0.250 mole) prepared as described above was added to pyridine-2-aldoxime (28.3 g, 0.227 mole) in dropwise manner over a period of 30 minutes (by adding one drop of bis-chloromethylether approximately every 0.5 second) at 45° C. with continuous stirring. Once the addition was complete, stirring was continued for three hours at the same temperature. The reaction mixture was then cooled to 18° C., and the product was filtered, washed with chloroform (66 g), and vacuum dried at 40° C. The product was again identified by proton NMR as 1-(2-hydroxyiminomethyl-1-pyridino)-3-(chloromethyl)-2-oxapropane, chloride salt, with 1,3-di-(2-hydroxyiminomethyl-1-pyridino)-2-oxapropane as an impurity (referred to herein as the "bis-impurity"). The yield was 56.4%, and from the NMR analysis, the product purity was 52.6%, with the bis-impurity as the remainder.

The addition of the pyridine-2-aldoxime to the bis-chloromethylether in accordance with the process of the invention thus resulted in a product of both significantly higher yield and purity as compared to the prior art process in which the bis-chloromethylether was added to the pyridine-2-aldoxime.

EXAMPLE 2

Illustrating This Invention: Conversion of 1-(2-Hydroxyiminomethyl-1-Pyridino)-3-(Chloromethyl)-2-Oxapropane, Chloride Salt, to 1-(2-Hydroxyiminomethyl-1-Pyridino)-3-(4-Carbamoyl-1-Pyridino)-2-Oxapropane, Dichloride Salt This example illustrates the conversion of 1-(2-hydroxyiminomethyl-1-pyridino)-3-(chloromethyl)-2-oxapropane, chloride salt, to 1-(2-hydroxyiminomethyl-1-pyridino)-3-(4-carbamoyl-1-pyridino)-2-oxapropane, dichloride salt. The structure of the latter is as follows:

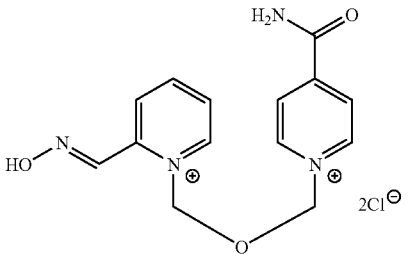

A 1-liter jacketed flask fitted with a mechanical stirrer, a temperature probe, a reflux condenser, and a positive nitrogen atmosphere was charged with 1-(2-hydroxyiminomethyl-1-pyridino)-3-(chloromethyl)-2-oxapropane, chloride salt (29.3 g, 0.124 mole) (as prepared by the procedure set forth in Example 1 in accordance with the invention), isonicotinamide (57.6 g, 0.472 mole) and N,N-dimethylformamide (600 mL). The slurry was heated to 35-40° C. and maintained at that temperature for 20 hours, then chilled to 0-5° C. The solids were then isolated by filtration, to yield a cake that was off-white in color. The cake was then washed with three 50-mL portions of isopropyl alcohol and dried in a vacuum oven at 40-50° C. to yield 45 g, representing a 95.7% yield, of a beige solid identified by proton NMR as 1-(2-hydroxyiminomethyl-1-pyridino)-3-(4-carbamoyl-1-pyridino)-2-oxapropane, dichloride salt. $^1$H-NMR (300 MHz, $D_2O$), δ, 6.14 (s, 2H, —$C\underline{H}_2OCH_2$), 6.27 (s, 2H, —$CH_2OC\underline{H}_2$), 7.97 (m, 1H), 8.33 (m, 3H), 8.36-8.53 (m, 2H), 8.9 (d, 1H), 9.05 (d, 2H) (aromatic protons and —C$\underline{H}$═NOH).

EXAMPLE 3

Illustrating This Invention: Conversion of 1-(2-Hydroxyiminomethyl-1-Pyridino)-3-(4-Carbamoyl-1-Pyridino)-2-Oxapropane, Dichloride Salt, to Dimethanesulfonate Salt This example illustrates the conversion of the dichloride salt produced by the procedure of Example 2 to the corresponding dimethanesulfonate salt, by ion exchange with alternative metallic salts of methanesulfonate. The structure of the dimethanesulfonate salt is as follows:

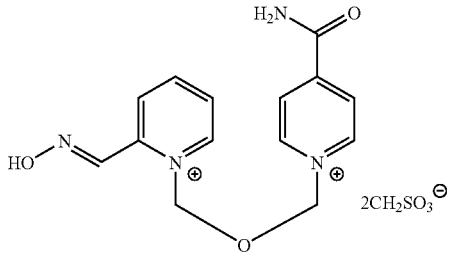

From silver methanesulfonate: A 250-mL jacketed flask fitted with a mechanical stirrer, a temperature probe, a reflux condenser, and a positive nitrogen atmosphere was charged with 1-(2-hydroxyiminomethyl-1-pyridino)-3-(4-carbamoyl-1-pyridino)-2-oxapropane, dichloride salt, as prepared in Example 2, (7.18 g, 0.020 mole), silver methanesulfonate (8.2 g, 0.040 mole), and a mixture of 90% methanol and 10% water (by weight) (160 g). The resulting slurry was heated to 50-60° C. and maintained at that temperature for 22 hours. A sample was then taken for reaction completion analysis by proton NMR), and the reaction mixture was chilled to 15-20° C. for work-up. The insolubles were filtered off and washed with two 20-mL portions of methanol. The combined filtrates were distilled under reduced pressure to a thick slurry (16.0 g) which was quenched with 180 mL denatured ethanol. The slurry was then further distilled under vacuum and then chilled to 0-5° C. The product was then isolated by filtration to yield a light purple solid, which was then washed with two 10-mL portions of denatured ethanol and dried to give 9.4 g of the crude dimethanesulfonate salt. The salt was then dissolved in 50 mL water, and the insolubles were filtered off and washed with 20 mL water. The combined filtrates were distilled under reduced pressure and solvent exchanged to ethanol. After water was removed, a slurry of tan color was formed and then chilled to 0-5° C. The solid was isolated by filtration, then washed with two 10-mL portions of denatured ethanol and dried to give 8.24 g (86.1% yield) of the dimethanesulfonate as a tan-colored solid.

From sodium methanesulfonate: The procedure of the preceding paragraph was repeated except that 2.7 g (7.52 mmoles) of the dichloride salt were used, sodium methanesulfonate (1.80 g, 15.24 mmoles) was used in place of the silver methanesulfonate, and 75 mL of methanol was used in place of the methanol-water mixture. The mixture was heated to reflux (65° C.) for 17 hours, and the product isolated and purified to yield 1.95 g (54.2% yield) as an off-white solid.

Via ion exchange resin: The ion exchange resin, AMBERLYST® (Dow Chemical Co., Midland, Mich., USA) A-26 (OH form) (6.0 g) was placed in a 125-mL Erlenmeyer flask and treated with 35 mL 1M methanesulfonic acid aqueous solution. The mixture was poured into a glass column ¾-inch in diameter. The solution was drained and the resin was rinsed with deionized water until the pH was 4.15. The dichloride salt of 1-(2-hydroxy-iminomethyl-1-pyridino)-3-(4-carbamoyl-1-pyridino)-2-oxapropane (1.0 g, 2.78 mmoles) was dissolved in water 6.5 g and the solution was passed through the resin bed at least five times. The resin bed was then eluted with 30 mL 0.5 mM methanesulfonic acid aqueous solution. After elution, the combined eluate was decolorized with 0.35 g activated charcoal, filtered through a bed of CELITE® (diatomaceous earth, product of Celite Corporation, Lompoc, Calif., USA), and distilled with ethanol under reduced pressure to remove water. The resulting residues were triturated with ethanol to give a light yellow slurry. After isolation, the cake was washed with 2×10 mL ethanol, and dried in vacuum oven to give HI-6 dimesylate 0.79 g (59.3% yield) as a light yellow solid.

EXAMPLE 4

Purification of 1-(2-Hydroxyiminomethyl-1-Pyridino)-3-(4-Carbamoyl-1-Pyridino)-2-Oxapropane, Dimethanesulfonate Salt with Charcoal The product of Example 3 (prepared by silver methanesulfonate) (8.23 g) was suspended in 60 mL of water in a 125-mL Erlenmeyer flask, where it was agitated with a mechanical stirrer. Insolubles were present, and charcoal (0.28 g) was added while stirring continued for 5 minutes. The resulting slurry was then filtered through a CELITE bed which was subsequently washed with two 10-mL portions of water. The filtrate was clear yellow in color and was distilled under reduced pressure. The solvent was then replaced with ethanol, and the resulting white slurry was chilled to 0-5° C. The solid product was isolated by filtration to yield an off-white solid, which was then washed with two 10-mL portions of denatured ethanol and dried in a vacuum oven at 40-50° C. to yield 7.74 g of pure 1-(2-hydroxyiminomethyl-1-pyridino)-3-(4-carbamoyl-1-pyridino)-2-oxapropane, dimethanesulfonate salt, representing a 94.0% recovery. $^1$H-NMR(300 MHz, $D_2O$): δ 2.82 (s, 6H, $CH_3SO_3$), 6.31 (s, 2H, —$CH_2O$), 6.43 (s, 2H,—$CH_2O$), 8.11(m,1H), 8.50 (m, 3H), 8.68 (m, 2H), 9.03, 9.05 (d, 1H), 9.22, 9.24 (d, 2H) (aromatic protons and —CH═N—OH); $^{13}$C NMR ($D_2O$): δ38.6, 85.8, 87.1, 126.9, 127.8, 128.1, 142.1, 144.7, 145.4, 147.2, 148.4, 151.0, 166.5; DSC (10° C./min): 163° C. (dec.).

EXAMPLE 5

Purification of 1-(2-Hydroxyiminomethyl-1-Pyridino)-3-(4-Carbamoyl-1-Pyridino)-2-Oxapropane, Dimethanesulfonate Salt with Mercaptopropyl-Functionalized Silica Gel In a parallel procedure to that of Example 4, 1.0 g of the product of Example 3, which was prepared by silver methanesulfonate and found to contain 1.0% residues (as silver ion) was dissolved in 9.6 mL of water in a 50-mL flask, where it was agitated with a mechanical stirrer. To the solution was added 1.0 g of 3-mercaptopropyl-functionalized silica gel (SiliCycle Inc., Quebec City, Quebec, Canada, and Sigma-Aldrich Corporation, St. Louis, Mo., USA). The resulting mixture was heated to 50-55° C. for three hours and filtered. After filtration, the silica gel was washed with 10 mL water. The aqueous filtrate was concentrated under reduced pressure to give a colorless oil which was then triturated with 20 mL ethanol to give a white slurry. The slurry was filtered to leave a white cake, which was washed with 10 mL of ethanol and dried to give 0.89 g (89% yield) of pure 1-(2-hydroxyiminomethyl-1-pyridino)-3-(4-carbamoyl-1-pyridino)-2-oxapropane, dimethanesulfonate salt, as a white solid. Thermogravimetric analysis (TGA) at 900° C. revealed that the solid contained less than 0.06% silver residues.

The foregoing is presented for purposes of illustration. Further variations and modifications that similarly employ or embody the features and concepts that define this invention will be readily apparent to those skilled in the art.

What is claimed is:

1. A process for the manufacture of a halide salt of a 1-(hydroxyiminomethyl-1-pyridino)-3-(halomethyl)-2-oxapropane, said process comprising adding a pyridinealdoxime having the formula

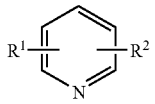

wherein $R^1$ is CH═NOH and $R^2$ is a member selected from the group consisting of H, lower alkyl, —C(O)—O-(lower alkyl), —C(O)—$NH_2$, and —CH═NOH, to a bis-halomethyl ether in liquid form *at ambient temperature or at a temperature within the range of about 30° C. to about 100° C. and* at a rate such that said bis-halomethyl ether remains in stoichiometric excess relative to said pyridinealdoxime during at least 75% of said addition, to yield a 1-(hydroxyiminomethyl-1-pyridino)-3-(halomethyl)-2-oxapropane, halide salt, of the formula

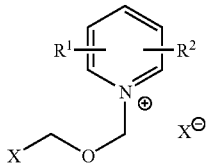

wherein X is a halogen atom.

2. A process for the manufacture of a halide salt of an asymmetrically substituted 1,3-di-(1-pyridino)-2-oxapropane, said process comprising:

(a) adding a pyridinealdoxime having the formula

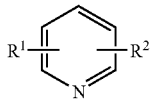

wherein $R^1$ is CH═NOH and $R^2$ a member selected from the group consisting of H, lower alkyl, —C(O)—O-(lower alkyl), —C(O)—$NH_2$, and —CH═NOH, to a bis-halomethyl ether in liquid form *at ambient temperature or at a temperature within the range of about 30° C. to about 100° C. and* at a rate such that said bis-halomethyl ether remains in molar excess relative to said pyridinealdoxime during at least 75% of said addition, to yield a 1-(hydroxyiminomethyl-1-pyridino)-3-(halomethyl)-2-oxapropane, halide salt, of the formula

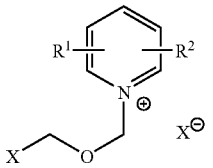

wherein X is a halogen atom, and (b) reacting said 1-(hydroxyiminomethyl-1-pyridino)-3-(halomethyl)-2-oxapropane, halide salt, with a substituted pyridine of the formula

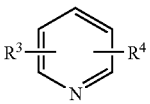

wherein $R^3$ and $R^4$ are members independently selected from the group consisting of H, lower alkyl, —C(O)—O-(lower alkyl), —C(O)—$NH_2$, and —CH═NOH, and $R^3$ and $R^4$ are not both identical to $R^1$ and $R^2$, to yield a halide salt of an asymmetrical 1-(hydroxyiminomethyl-1-pyridino)-3-(1-pyridino)-2-oxapropane having the formula

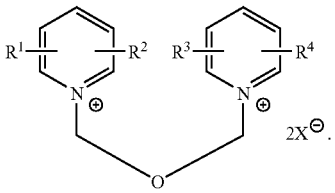

3. A process for the manufacture of a salt of an asymmetrically substituted 1,3-di-(1-pyridino)-2-oxapropane having the formula

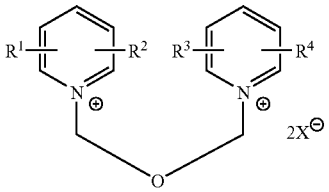

wherein $R^1$ is —CH═NOH, $R^2$ a member selected from the group consisting of H. lower alkyl, —C(O)—O-(lower alkyl), —C(O)—$NH_2$ and —CH═NOH, and $R^3$ and $R^4$ are members independently selected from the group consisting of H. lower alkyl, —C(O)—O-(lower alkyl), —C(O)—$NH_2$, and —CH═NOH, in which the anion Y of said salt is a pharmaceutically acceptable anion other than a halide ion, said process comprising converting a halide salt of said asymmetrically substituted 1,3-di-(1-pyridino)-2-oxapropane by ion exchange between said halide salt and a salt of said pharmaceutically acceptable anion.

4. The process of claims 1, 2 or 3 wherein said pyridinealdoxime has the formula

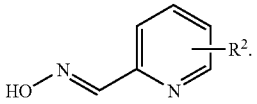

5. The process of claims 1, 2 or 3 wherein said pyridinealdoxime has the formula

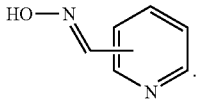

6. The process of claims 1, 2 or 3 wherein said pyridinealdoxime has the formula

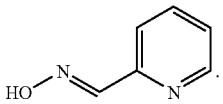

7. The process of claims 2 or 3 wherein said substituted pyridine has the formula

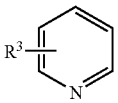

wherein $R^3$ is other than H.

8. The process of claims 2 or 3 wherein said substituted pyridine has the formula

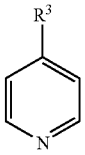

wherein $R^3$ is other than H.

9. The process of claims 2 or 3 wherein said substituted pyridine has the formula

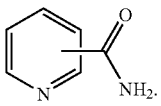

10. The process of claims 2 or 3 wherein said substituted pyridine has the formula

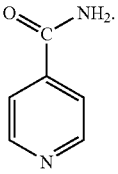

11. The process of claims 2 or 3 wherein said pyridinealdoxime has the formula

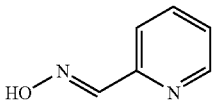

wherein $R^3$ is other than H, and said substituted pyridine has the formula

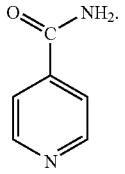

12. The process of claim 3 in which said pharmaceutically acceptable anion is a hydrocarbylsulfonate or halohydrocarbylsulfonate ion of the formula $R^5SO_3$— wherein $R^5$ is a member selected from the group consisting of aliphatic, haloaliphatic, cycloaliphatic, halocycloaliphatic, aromatic, and haloaromatic.

13. The process of claim 12 wherein $R^5$ is a member selected from the group consisting of $C_1$-$C_4$ alkyl, halo-$C_1$-$C_4$ alkyl, cyclohexyl, and phenyl.

14. The process of claim 12 wherein $R^5$ is $C_1$-$C_4$ alkyl.

15. The process of claim 12 wherein $R^5$ is methyl.

16. The process of claim 1 wherein X is Br or Cl.

17. The process of claim 1 wherein X is Cl.

18. The process of claims 2 or 3 wherein said reaction between said 1-(2-hydroxyiminomethyl-1-pyridino)-3-(halomethyl)-2-oxapropane, halide salt, and said substituted pyridine is performed in a solvent selected from the group consisting of a tetrahalomethane, dimethylformamide, dimethylsulfoxide, a trihalomethane, a dihalomethane, N,N-dimethylacetamide, 1-methyl-2-pyrrolidone, acetonitrile, dioxane, tetrahydrofuran, and 2-methyltetrahydrofuran.

19. The process of claim 1 wherein said bis-halomethyl ether remains in molar excess relative to said 2 pyridinealdoxime during at least 90% of said addition.

20. The process of claim 1 wherein said 2-pyridinealdoxime is added in dropwise manner to said bis-halomethyl ether during agitation of said bis-halomethyl ether.

*21. The process of claim 1 comprising adding said pyridinealdoxime to said bis-halomethyl ether at a temperature within the range of about 30° C. to about 100° C.*

*22. The process of claim 1 comprising adding said pyridinealdoxime to said bis-halomethyl ether at a temperature within the range of about 35° C. to about 60° C.*

* * * * *